US006190645B1

(12) United States Patent
SaNogueira et al.

(10) Patent No.: US 6,190,645 B1
(45) Date of Patent: Feb. 20, 2001

(54) SUNSCREEN FOR THE SCALP HAIR AND HAIR

(75) Inventors: James SaNogueira, Suffern, NY (US); Thomas Russo, Newton, NJ (US)

(73) Assignee: Playtex Products, Inc., Westport, CT (US)

( * ) Notice: Under 35 U.S.C. 154(b), the term of this patent shall be extended for 0 days.

(21) Appl. No.: 09/354,117

(22) Filed: Jul. 15, 1999

(51) Int. Cl.[7] .............................. A61K 7/42; A61K 7/44; A61K 7/06; A61K 7/00

(52) U.S. Cl. .......................... 424/59; 424/60; 424/70.1; 424/70.9; 424/400; 424/401

(58) Field of Search .............................. 424/59, 60, 70.1, 424/70.9, 400, 401

(56) References Cited

U.S. PATENT DOCUMENTS

| 5,208,011 | 5/1993 | Vaughan | 424/59 |
| 5,601,811 | 2/1997 | Gallagher et al. | 424/709 |
| 5,609,854 | 3/1997 | Guerrero et al. | 424/59 |
| 5,616,331 | 4/1997 | Allard et al. | 424/401 |
| 5,681,554 | 10/1997 | Cannell et al. | 424/70.14 |
| 5,776,438 | 7/1998 | Tokue et al. | 424/59 |
| 5,843,411 | 12/1998 | Hernandez et al. | 424/59 |

*Primary Examiner*—Shelley A. Dodson
(74) *Attorney, Agent, or Firm*—Ohlandt, Greeley, Ruggiero & Perle, LLP

(57) ABSTRACT

The present invention is a sunscreen composition that protects the scalp and hair from the sun's rays. The composition contains at least one sunscreen agent in combination with a cinnamido alkyl amine cationic quaternary salt. In addition, a method for protecting the scalp and hair by applying an effective amount of the composition is provided.

28 Claims, No Drawings

SUNSCREEN FOR THE SCALP HAIR AND HAIR

BACKGROUND OF THE INVENTION

I. Field of the Invention

The present invention relates to sunscreens. More particularly, the present invention relates to sunscreens that protect the scalp and hair from the damaging effects of sunlight.

II. Description of the Prior Art

Sunscreen compositions are applied to the skin to protect the skin from the sun's ultraviolet rays that can lead to erythema, a reddening of the skin also known as sunburn. Sunlight or ultraviolet radiation in the UV-B range has a wavelength of 290 nm to 320 nm and is known to be the primary cause of sunburn. While, ultraviolet rays at a wavelength of 320 nm to 400 nm, known as UV-A radiation, produces tanning of the skin. However, in the process of doing so, the UV-A rays can damage or harm the skin.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

In general, sunscreen compositions are oil and water emulsions. In this system, the UV-absorbing compounds are typically incorporated into the oil phase.

Sunscreens may also include physical or inorganic metal oxides that block the sun's rays. Titanium dioxide and zinc oxide are commonly used for this purpose.

As stated above, sunscreens are typically formulated with the goal of inhibiting skin damage from the sun's rays. The sunscreen composition filters or blocks the harmful UV-A and UV-B rays that can damage and harm the skin. It is believed that sunscreen agents accomplish this by absorbing the UV-A and/or UV-B rays.

However, the skin is not the only area that can be harmed by the sun's rays. Hair can also suffer damage from excessive exposure to the sun. For example, the hair cuticle can be damaged, which leads to a split end. In addition, the hair can become brittle and dry and also experience color fading.

Consumers consider many factors when purchasing a sunscreen product. One of the most important considerations is the sun protection factor (SPF). This determines the amount of protection that the sunscreen composition provides over a given period of time. There are many to choose from and selection will be based upon the consumer's needs. The consumer also gives consideration to the substantivity of the product, that is how durable is the product after applying it. This effects how often the composition will need to be applied when the consumer is out in the sun. A third consideration is product feel and how well the product spreads. Typically, consumers want a product that feels smooth and silky. Another factor is the shelf life of the product, which is determined by the chemical and physical stability of the sunscreen composition. In addition, product form will also play a part since there is a variety of choices such as lotions, gels, creams, sprays, and aerosols that are available.

However, if the consumer is searching for a sunscreen product that protects the scalp and hair from ultraviolet irradiation, he or she will be forced to use a sunscreen product that is meant to be applied on the skin. The result is that the scalp may be protected, but the hair may not be. As such, there is a need to provide the consumer with a sunscreen product that is specifically formulated to provide protection to both the scalp and hair from the damaging effects of the sun that can lead to color fade, dryness, and cutical separation. Furthermore, the product provides the additional benefit of imparting grooming and styling benefits.

U.S. Pat. No. 5,681,554 claims a cosmetic composition for treating hair that contains a hydrolyzed protein comprising anionic and cationic amino acids, a divalent cationic compound, a vitamin compound, and a cosmetic carrier.

U.S. Pat. No. 5,616,331 claims a topically applicable sunscreen/cosmetic composition for the photoprotection of human skin and/or hair against the damaging effects of UV-A and/or UV-B irradiation. The composition is an ultrafine oil-in-water emulsion of homogeneously and finely dispersed particulates of an inorganic nanopigment of a metal oxide, such as titanium dioxide. The average particle size of the globules in the oily phase is in the range from 100 nm to 1,000 nm.

U.S. Pat. No. 5,601,811 discloses cinnamido amine cationic quaternary salts that have UV-absorbing properties. These compounds are soluble in water and when used in formulations, typically will improve skin feel by reducing the greasy, oily feel that one normally finds.

BRIEF SUMMARY OF THE INVENTION

It is an object of the present invention to provide a sunscreen composition that protects both the scalp and hair from sun damage.

It is another object of the present invention to provide such a sunscreen composition that provides photoprotection to the skin, in particular the scalp and hair, from the sun.

It is still another object of the present invention to provide such a sunscreen composition that combines a sunscreen agent with a water soluble UV-absorbing agent.

It is still yet another object of the present invention to provide such a sunscreen composition that provides a grooming and styling benefit for added control.

It is a further object of the present invention to provide a method of protecting the scalp and hair from damaging sunlight.

To accomplish the foregoing objects and advantages, the present invention, in brief summary, is a sunscreen composition that is formulated to provide protection to the scalp and hair. The composition contains at least one sunscreen agent and a cinnamido alkyl amine cationic quaternary salt. In a preferred embodiment, the sunscreen composition also contains an emulsifier, a solvent, a pH adjuster, and a preservative/antioxidant.

The present invention also includes a method for protecting the scalp and hair from damaging sunlight, whereby an effective amount of a composition comprising at least one sunscreen agent and a cinnamido alkyl amine cationic quaternary salt is applied to the scalp and hair.

DETAILED DESCRIPTION OF THE INVENTION

The present invention is a sunscreen composition that protects the scalp and hair from the damaging effects of sunlight. The composition comprises at least one sunscreen agent and a cinnamido alkyl amine cationic quaternary salt.

Sunscreen agents

The sunscreen agents that can be used in the present invention must be capable of absorbing or blocking the harmful effects of ultraviolet radiation. In addition, they must be non-toxic and non-irritating when applied to the skin, such as the scalp, and hair.

Suitable sunscreen agents include, for example, para-aminobenzoic acid (PABA), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, or mixtures thereof. The preferred sunscreen agents are octyl methoxycinnamate, octyl salicylate, benzophenone-3, or mixtures thereof.

The sunscreen agents are added at about 1.0 wt. % to 40 wt. % of the total composition. The amount of sunscreen agent in the composition will vary in the above range dependent upon the sun protection factor (SPF) desired. Normally, the higher the SPF, the greater the total amount of sunscreen agents. Preferably, the sunscreen agents are included at about 1.4 wt. % to 30.0 wt. %.

Cinnamido Alkyl Amine Cationic Quaternary Salt

An essential component of the present invention is a cinnamido alkyl amine cationic quaternary salt compound. This compound conveniently is soluble and dispersible in water and imparts grooming and styling benefits to the composition. Moreover, the compound has cationic and UV absorbing properties. The preferred cinnamido alkyl amine cationic quaternary salt is cinnamidopropyl trimethyl ammonium chloride, which is sold under the tradename INCROQUAT-UV-283 manufactured by Croda, Inc.

Typically, the cinnamido alkyl amine cationic quaternary salt is about 0.1 wt. % to about 5.0 wt. % of the present invention. Preferably, about 0.5 wt. % to about 1.5 wt. % is added.

Water

The composition of the present invention, may optionally, have up to about 98 wt. % water. Preferably, from about 5 wt. % to about 90 wt. % water.

Solvents

The present invention may contain a solvent, such as alcohol, cyclomethicone, organo functional silicones, and mixtures thereof, which help incorporate the sunscreen agents, and cinnamido alkyl amine cationic salt into the composition.

A preferred solvent is SD alcohol 40, which is ethyl alcohol that is denatured with t-butyl alcohol in combination with brucine, brucine sulfate, or quassin. This component is critical if it is desired that the composition be clear. However, clarity is desired, but not a requirement of the present invention. Up to about 98 wt. % of solvent may be added to the composition. Preferably, about 50 wt. % to about 90 wt. % of solvent is used.

Film Formers

The present invention may also include one or more film formers. For example, an ethyl ester of PVM/MA copolymer, PVP/Dimethiconylacrylate/Polycarbamyl/Polyglycol ester, Glycerin/Diethylene Glycol/Adipate copolymer, PVP/Eicosene copolymer, and mixtures thereof may be added to the present invention to form a film that remains after the volatile components have evaporated.

The film former may be added in an amount about 0.1 wt. % to about 15.0 wt. % of the total weight of the present invention. Preferably, about 0.1 wt. % to about 2.0 wt. % of film formers may be used.

pH Adjusters

The pH of the composition of the present invention is about 3.0 to about 8.0. Preferably, the pH is about 5.5 to about 6.0. This may be maintained or adjusted by optionally adding a pH adjuster or chelating agent. For example, aminomethyl propanol, sodium hydroxide, triethanolamine, and trisodium ethylenediaminetetraacetic acid, and mixtures thereof are suitable pH adjusters in the present invention.

pH adjusters may be added at about 0.01 wt. % to about 5.0 wt. % in the composition of the present invention. Preferably, about 0.01 wt. % to about 2.0 wt. % is added.

Emulsifiers

An emulsifier may also be added to the present invention. The emulsifier enables two or more immiscible liquids to be combined homogeneously, while increasing the viscosity of the composition. Moreover, an emulsifier acts to stabilize the composition. One or more emulsifiers that can be used in the present invention include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, sodium glyceryl oleate phosphate, hydrogenated vegetable glycerides phosphate and mixtures thereof.

Furthermore, one or more synthetic polymers may be used as an emulsifier. For example, PVP Eicosene copolymer, acrylates/$C_{10}$–$C_{30}$ alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are sorbitan oleate, acrylates/steareth-20 methacrylate copolymer, and mixtures thereof.

The emulsifier is used at about 0.1 wt. % to about 10.0 wt. % of the total weight of the composition of the present invention. Preferably, about 0.5 wt. % to about 3.0 wt. % of emulsifiers are used in the present invention.

Emollients

The present composition may additionally contain other ingredients, such as one or more emollients. An emollient provides a softening or soothing effect on the skin surface and is generally considered safe for topical use. It also helps control the rate of evaporation and the tackiness of the composition. Preferred emollients include mineral oil, lanolin oil, coconut oil, cocoa butter, olive oil, aloe extracts, jojoba oils, castor oil, fatty acids such as oleic and stearic, fatty alcohols such as cetyl and hexadecyl (ENJAY), diisopropyl adipate, hydroxybenzoate esters, benzoic acid esters of $C_9$–$C_{15}$ alcohols, isononyl iso-nonanoate, alkanes such as mineral oil, silicones such as dimethyl polysiloxane, ether such as polyoxypropylene butyl ethers and polyoxypropylene cetyl ethers, and $C_{12}$–$C_{15}$ alkyl benzoate. The preferred emollients are hydroxybenzoate esters and $C_{12}$–$C_{15}$ alkyl benzoates.

The total amount of emollients in the present composition is about 0.1 wt. % to about 2.0 wt. % of the total weight of the composition.

Preservatives/Antioxidants

Optionally, one or more preservatives/antioxidants may be added to the composition of the present invention. Compounds such as diazolidinyl urea, iodopropynyl butylcarbamate, vitamin E, vitamin E acetate, vitamin C, butylated hydroxytoluene, methylparaben, and mixtures thereof may be added as a preservative/antioxidant.

About 0.01 wt. % to about 2.0 wt. % of preservatives/antioxidants may be added to the composition of the present invention.

Optional Additives

The sunscreen composition of the present invention may also contain optional additives. For instance, a fragrance, colorant, plant extract, absorbent, viscosity modifier, waterproofing agent, styling gel, and mixtures thereof, may be added.

Process

The process used to manufacture the composition of the present invention must be capable of forming a homogeneous composition. The present invention may be prepared by using techniques and methods well known in the art. In general, ingredients are incorporated by mixing and applying heat if necessary, until the composition is uniform and homogeneous. The composition may be homogenized to ensure homogeneity.

The external preparation according to the present invention may take any given form. For example, it may be a lotion, cream, an ointment, a gel, a dispersant or an aerosol.

The present invention includes a method for protecting the scalp and hair from damaging sunlight. The method comprises the steps of applying an effective amount of a composition comprising at least one sunscreen agent and cinnamido alkyl amine cationic quaternary salt.

Having thus described the present invention with particular reference to preferred embodiments thereof, it will be apparent that various changes and modifications may be made therein without departing from the spirit and scope of the invention as defined in the appended claims.

What is claimed is:

1. A sunscreen composition for protecting hair comprising:
   at least one sunscreen agent; and
   a cinnamido alkyl amine cationic quaternary salt.

2. The composition of claim 1, wherein said sunscreen agent is selected from the group consisting of benzophenone-3, benzophenone-6, benzophenone-8, benzophenone-12, octyl methoxycinnamate, octyl salicylate, homosalate, methyl anthranilate, octocrylene, red petrolatum, and mixtures thereof.

3. The composition of claim 1, wherein said sunscreen agent is about 1.4 wt. % to about 30 wt. % of the total weight of the composition.

4. The composition of claim 1, wherein said cinnamido alkyl amine cationic quaternary salt is about 0.1 wt. % to about 5.0 wt. % of the total weight of the composition.

5. The composition of claim 1, wherein said cinnamido alkyl amine cationic quaternary salt is cinnamidopropyl trimethyl ammonium chloride.

6. The composition of claim 1, further comprising a solvent in an amount up to about 98 wt. % of the total weight of the composition.

7. The composition of claim 6, wherein said solvent is selected from the group consisting of alcohol, cyclomethicone, organo functional silicones, and mixtures thereof.

8. The composition of claim 1, further comprising water in an amount up to about 98 wt. % of the total weight of the composition.

9. The composition of claim 1, further comprising a film former.

10. The composition of claim 9, wherein said film former is about 0.1 wt. % to about 15.0 wt. % of the total weight of the composition.

11. The composition of claim 9, wherein said film former is selected from the group consisting of an ethyl ester of PVM/MA copolymer, PVP/Dimethiconylacrylate/Polycarbamyl/Polyglycol ester, Glycerin/Diethylene Glycol/Adipate copolymer, PVP/Eicosene copolymer, and mixtures thereof.

12. The composition of claim 1, further comprising a pH adjuster.

13. The composition of claim 12, wherein said pH adjuster is about 0.01 wt. % to about 5.0 wt. % of the total weight of the composition.

14. The composition of claim 12, wherein said pH adjuster is selected from the group consisting of aminomethyl propanol, sodium hydroxide, triethanolamine, trisodium ethylenediaminetetraacetic acid, and mixtures thereof.

15. The composition of claim 1, further comprising an emulsifier.

16. The composition of claim 15, wherein said emulsifier is about 0.1 wt. % to about 10.0 wt. % of the total weight of the composition.

17. The composition of claim 15, wherein said emulsifier is selected from the group consisting of PVP Eicosene copolymer, cetyl phosphate, sorbitan isostearate, acrylates/$C_{10}$–$C_{30}$ alkyl acrylate crosspolymer, PEG-20 sorbitan isostearate, and mixtures thereof.

18. The composition of claim 1, further comprising an emollient.

19. The composition of claim 18, wherein said emollient is selected from the group consisting of hydroxybenzoate esters, $C_{12}$–$C_{15}$ alkyl benzoates, aloe vera, and mixtures thereof.

20. The composition of claim 1, further comprising a preservative/antioxidant.

21. The composition of claim 20, wherein said preservative/antioxidant is selected from the group consisting of diazolidinyl urea, iodopropynyl butylcarbamate, vitamin E, vitamin E acetate, vitamin C, butylated hydroxytoluene, methylparaben, and mixtures thereof.

22. The composition of claim 1, further comprising optional ingredients selected from the group consisting of fragrances, colorants, plant extracts, absorbents, viscosity modifiers, waterproofing agents, styling gels, and mixtures thereof.

23. A sunscreen composition for protecting hair comprising:
   a sunscreen agent;
   a cinnamido alkyl amine cationic quaternary salt;
   a solvent;
   a film former;
   a pH adjuster; and
   water.

24. The composition of claim 23, wherein said suncreen agent is present in an amount about 1.4 wt. % to about 30 wt. % of the total weight of the composition, wherein said cinnamido alkyl amine cationic quaternary salt is present in an amount about 0.1 wt. % to about 5 wt. %, and wherein said solvent and water are each present in an amount up to about 98 wt. %.

25. A method for protecting hair from damaging sunlight, comprising the step of:
   applying an effective amount of a composition comprising at least one sunscreen agent and a cinnamido alkyl amine cationic quaternary salt to the hair.

26. The composition of claim 2, wherein said sunscreen agent is selected from the group consisting of benzophenone-3, benzophenone-6, benzophenone-8, benzophenone-12, homosalate, methyl anthranilate, octocrylene, red petrolatum, and mixtures thereof.

27. The composition of claim 7, wherein said solvent is selected from the group consisting of cyclomethicone, organo functional silicones, and mixtures thereof.

28. The composition of claim 7, wherein said alcohol is SD alcohol 40.

* * * * *

UNITED STATES PATENT AND TRADEMARK OFFICE
CERTIFICATE OF CORRECTION

PATENT NO. : 6,190,645 B1
DATED : February 20, 2001
INVENTOR(S) : James SaNogueira & Thomas Russo It is certified that error appears in the above-identified patent and that said Letters Patent is hereby corrected as shown below:

Title page:
Item (54) (the title of the invention) reads: SUNSCREEN FOR THE SCALP AND HAIR Signed and Sealed this Twenty-fifth Day of September, 2001

Attest:

*Attesting Officer*

NICHOLAS P. GODICI
*Acting Director of the United States Patent and Trademark Office*